United States Patent
Bleck (10) Patent No.: US 10,065,351 B2
(45) Date of Patent: Sep. 4, 2018

(54) MELT TEMPERATURE MEASUREMENT SYSTEM

(71) Applicant: Procon Training and Consulting, LLC, Phillips, WI (US)

(72) Inventor: Richard A. Bleck, Phillips, WI (US)

(73) Assignee: Procon Training and Consulting, LLC, Phillips, WI (US)

(*) Notice: Subject to any disclaimer, the term of this patent is extended or adjusted under 35 U.S.C. 154(b) by 227 days.

(21) Appl. No.: 15/227,741

(22) Filed: Aug. 3, 2016

(65) Prior Publication Data

US 2018/0036929 A1  Feb. 8, 2018

(51) Int. Cl.
| | |
|---|---|
| G01N 25/00 | (2006.01) |
| B29C 45/78 | (2006.01) |
| G01N 25/04 | (2006.01) |
| G01K 1/14 | (2006.01) |
| G01K 13/02 | (2006.01) |

(52) U.S. Cl.
CPC ............ B29C 45/78 (2013.01); G01K 1/14 (2013.01); G01K 13/02 (2013.01); G01N 25/04 (2013.01); B29C 2945/7604 (2013.01); B29C 2945/7618 (2013.01); B29C 2945/76287 (2013.01); B29C 2945/76381 (2013.01); G01K 2013/026 (2013.01)

(58) Field of Classification Search
CPC combination set(s) only.
See application file for complete search history.

(56) References Cited

U.S. PATENT DOCUMENTS

| | | | | |
|---|---|---|---|---|
| 6,299,348 B1 * | 10/2001 | Theuwis | ................ | G01K 7/025 136/226 |
| 6,859,482 B1 * | 2/2005 | Strowitzki | .............. | H01S 3/038 372/55 |
| 7,832,294 B2 * | 11/2010 | Neyens | ................ | G01N 33/206 73/866.5 |

FOREIGN PATENT DOCUMENTS

| | | |
|---|---|---|
| EP | 0 552 684 A1 | 7/1993 |
| EP | 3 012 606 A1 | 4/2016 |
| WO | WO-2015/069977 A1 | 5/2015 |

OTHER PUBLICATIONS

International Search Report and Written Opinion, PCT/US2017/044665, Procon Training and Consulting, LLC, 13 pages, (dated Oct. 9, 2017).

* cited by examiner

*Primary Examiner* — Manish S Shah
*Assistant Examiner* — Nasir U Ahmed
(74) *Attorney, Agent, or Firm* — Foley & Lardner LLP (57) ABSTRACT

A melt temperature sensing kit includes a housing and a cup. The housing defines a cavity and has an outer periphery configured to be received by a platen of an injection molding machine. The cup has a proximate end and a distal end and is configured to be received within at least a portion of the cavity. The cup includes a base enclosing the distal end of the cup and a sidewall extending from the base, the sidewall defining a first aperture at the proximate end of the cup, a second aperture disposed between the proximate end and the distal end of the cup, and an internal volume. The first aperture, the second aperture, and the internal volume cooperate to define a flow path. At least one of the housing and the cup facilitate measurement of a shot flow temperature as part of a melt temperature measurement process.

10 Claims, 5 Drawing Sheets

MELT TEMPERATURE MEASUREMENT SYSTEM

BACKGROUND

Injection molded products may have characteristics (e.g., impact strength, tensile strength, etc.) that vary based on the temperature of the material during the initial production of the injection molded product. Accurate measurement of the temperature of the material during the initial production of the injection molded product is important in the production of injection molded products having desired characteristics. Traditional systems for measuring the temperature of the material are inaccurate at least due to the temperature variations in the shot flow induced by heat transfer into one or more components of the injection molding machine and/or the measurement system.

SUMMARY

One exemplary embodiment relates to a melt temperature sensing kit. The melt temperature sensing kit includes a housing and a cup. The housing defines a cavity and has an outer periphery configured to be received by a platen of an injection molding machine. The cup has a proximate end and a distal end and is configured to be received within at least a portion of the cavity. The cup includes a base enclosing the distal end of the cup and a sidewall extending from the base, the sidewall defining a first aperture at the proximate end of the cup, a second aperture disposed between the proximate end and the distal end of the cup, and an internal volume. The first aperture, the second aperture, and the internal volume cooperate to define a flow path. At least one of the housing and the cup are configured to position a temperature probe along the flow path and thereby facilitate measurement of a shot flow temperature as part of a melt temperature measurement process.

Another exemplary embodiment relates to a melt temperature test cup that includes a base and a sidewall. The sidewall has a proximate end that defines a first aperture and a distal end coupled to the base. The sidewall defines a second aperture disposed between the proximate end and the distal end and an internal volume. The first aperture, the second aperture, and the internal volume cooperatively define a flow path. At least one of the base and the sidewall is configured to be received by a housing of a melt temperature sensing kit and thereby facilitate measurement of a shot flow temperature as part of a melt temperature measurement process.

Still another exemplary embodiment relates to a melt temperature measurement process that includes assembling a melt temperature sensing kit, the melt temperature sensing kit including a temperature probe, inserting the melt temperature sensing kit into a platen of an injection molding machine, providing a shot flow through the melt temperature sensing kit with the injection molding machine, and measuring a shot flow temperature of the shot flow with the temperature probe of the melt temperature sensing kit.

The invention is capable of other embodiments and of being carried out in various ways. Alternative exemplary embodiments relate to other features and combinations of features as may be recited herein.

BRIEF DESCRIPTION OF THE DRAWINGS

The disclosure will become more fully understood from the following detailed description, taken in conjunction with the accompanying figures, wherein like reference numerals refer to like elements, in which.

DETAILED DESCRIPTION

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

According to an exemplary embodiment, a melt temperature sensing kit facilitates the measurement of a melt temperature of a material (e.g., a polymer, etc.) as part of an injection molding process. In one embodiment, the melt temperature sensing kit facilitates the measurement of the melt temperature of the material during the injection molding process. The melt temperature sensing kit includes a housing configured to be received by one or more components of an injection molding machine. By way of example, the injection molding machine may include a locating ring associated with a stationary platen. The housing may be configured to be received by the locating ring. The locating ring may receive a barrel and/or a nozzle of the injection molding machine when the housing of the melt temperature sensing kit is removed therefrom.

A cup of the melt temperature sensing kit is disposed within the housing and receives a shot flow (e.g., a liquid or molten volume of material provided by the barrel and/or nozzle of the injection molding machine, etc.). In one embodiment, the cup is configured to maintain the liquidity of at least a portion of the shot flow to facilitate a temperature measurement by a temperature probe. The temperature probe measures the temperature of the shot flow as it passes through the melt temperature sensing kit (i.e., measures the shot flow temperature). The melt temperature sensing kit facilitates measuring the temperature of the shot flow under conditions that are similar to (e.g., identical to, etc.) the conditions under which the injection molding machine produces injection molded products (e.g., a heater band setting, an injection pressure, a back pressure, a residence time, a screw RPM, and/or a screw-design-related condition equal to that of the injection molding machine during the production of injection molded products, with a temperature measurement location within the platen rather than on a bed or table of the injection molding machine, etc.).

The actual melt temperature of the material may not be equal to the heater band setting of the injection molding machine. Applicant has discovered that approximately 30 percent of the temperature of the shot flow is produced by the heater bands of the injection molding machine and that the remaining 70 percent of the temperature is produced by interaction of the RPM of the screw, back pressure, screw design, and/or residence time in the barrel between successive shots. The melt temperature sensing kit provides temperature measurements that are more accurate than those produced by traditional melt temperature measurement techniques (e.g., due to the cup keeping the shot flow liquid or molten for longer, due to the measurement location, due to the melt temperature measurement conditions, etc.).

Figure 1:
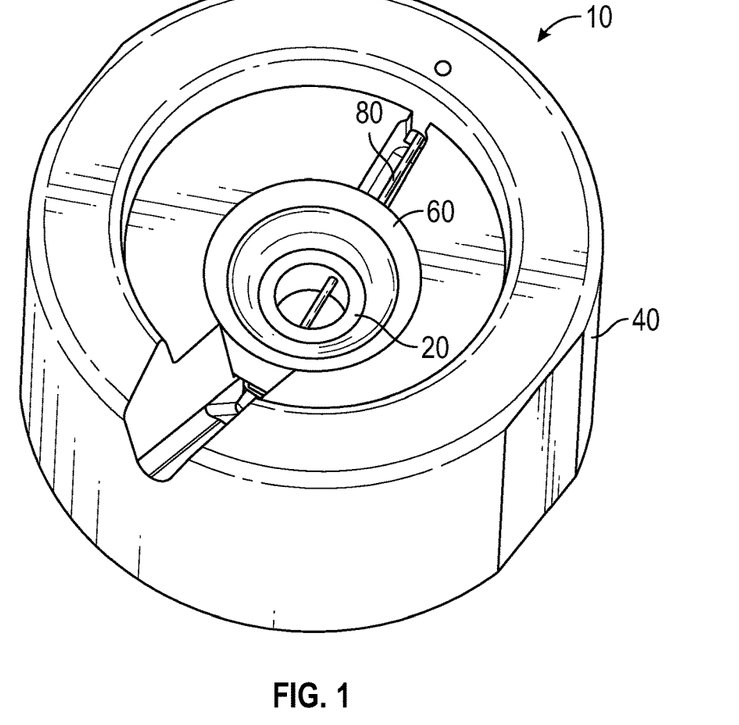
FIG. 1 is a perspective view of a melt temperature sensing kit, according to an exemplary embodiment.
Figure 2:
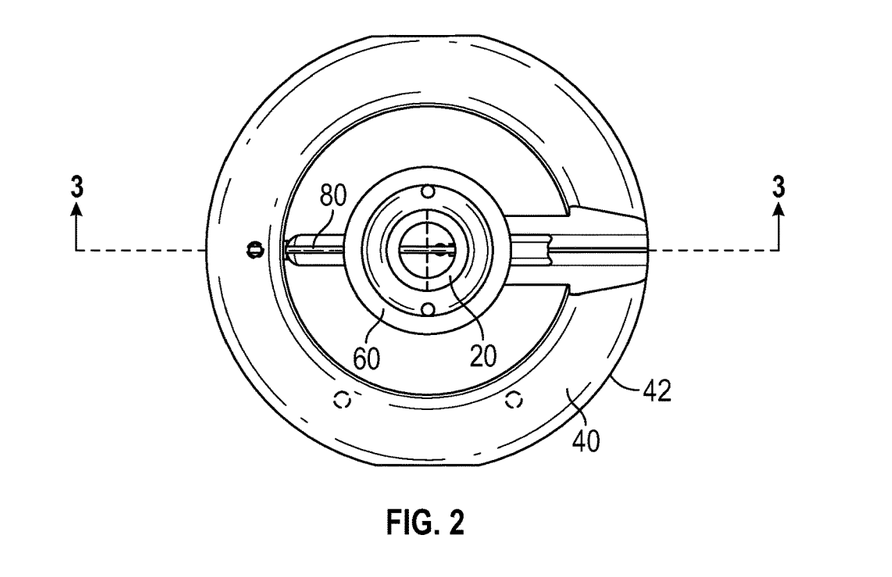
FIG. 2 is a top plan view of the melt temperature sensing kit of FIG. 1, according to an exemplary embodiment.
Figure 3:
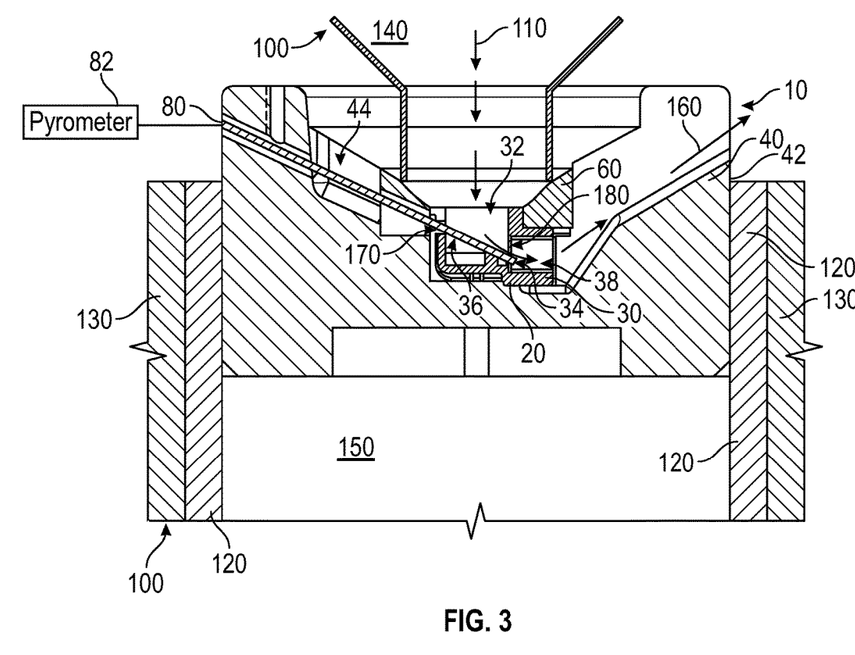
FIG. 3 is a sectional view of the melt temperature sensing kit of FIG. 1 provided with an injection molding machine, according to an exemplary embodiment.

According to the exemplary embodiment shown in FIGS. 1-3, a melt temperature sensing kit, shown as melt temperature sensing kit 10, facilitates measurement of a shot flow temperature as part of a melt temperature measurement process. A target melt temperature or a target melt temperature range may be retrieved (e.g., by an operator from a lookup table, from a memory, etc.), and one or more operating conditions of the particular injection molding machine may be adjusted (e.g., iteratively, etc.) such that the shot flow temperature as measured by the melt temperature sensing kit 10 approaches, equals, or falls within the target melt temperature or the target melt temperature range. As shown in FIGS. 1-3, the melt temperature sensing kit 10 includes a cup, shown as cup 20, a housing, shown as housing 40, and a locator, shown as locator 60. In other embodiments, the melt temperature sensing kit 10 does not include the locator 60.

At least one of the housing 40 and the cup 20 are configured to position a temperature probe, shown as temperature probe 80, along a flow path defined at least partially by the housing 40 and/or the cup 20. The temperature probe 80 may be and/or include a high speed probe thermometer. As shown in FIG. 3, a digital thermometer, shown as pyrometer 82, is coupled to the temperature probe 80. The pyrometer 82 may be used (e.g., by an operator, etc.) to read and/or record a maximum shot flow temperature. By way of example, the pyrometer 82 may display and/or record the maximum temperature observed by the temperature probe 80. The maximum temperature observed by the temperature probe 80 may correspond with (e.g., equal, etc.) the maximum shot flow temperature. In one embodiment, the melt temperature sensing kit 10 includes the pyrometer 82. In one embodiment, the melt temperature sensing kit 10 includes the temperature probe 80. In other embodiments, the temperature probe 80 and/or the pyrometer 82 is independently provided (e.g., provided by an operator, etc.).

The temperature probe 80 may include a stop configured to interface with the housing 40 and thereby limit insertion of the temperature probe 80 to a target depth. By way of example, the stop may be coupled to the temperature probe 80 (e.g., with a set screw, etc.). By way of another example, the stop may be integrally formed with the temperature probe 80 (e.g., as a projection extending from a body of the temperature probe 80, etc.), among other alternatives. In other embodiments, the cup 20 is configured to provide a stop against which the temperature probe 80 engages to set the insertion depth of the temperature probe 80 to a target depth. In some embodiments, the melt temperature sensing kit 10 includes a fastener (e.g., a thumb screw, etc.) configured to hold the temperature probe 80 in position. By way of example, the fastener may include a screw that threadingly engages with an aperture defined by the housing 40. The screw may be threaded into the housing 40 until it engages the temperature probe 80, holding the temperature probe 80 in position.

As shown in FIG. 3, an injection molding machine 100 produces injection molded products by providing a shot flow (e.g., a liquid or molten volume of material, etc.), shown as shot flow 110, having a shot flow temperature. Applicant has discovered that the shot flow temperature, as measured using the melt temperature sensing kit 10, approaches or equals the melt temperature of the material. Accurate measurement of the melt temperature of the material is important for the reliable production of quality injection molded products at least because the strength of the injection molded product and/or the flow characteristics of the material through the mold is highly dependent on the melt temperature of the material during initial manufacture.

According to an exemplary embodiment, the cup 20 facilitates measurement of the shot flow temperature. The cup 20 is configured to facilitate keeping the shot flow 110 provided by the injection molding machine 100 liquid or molten for an extended period of time following a shot initiation time (e.g., the time at which the material is first provided into the melt temperature sensing kit 10 by the injection molding machine 100, etc.). The cup 20 is thereby configured to facilitate accurately measuring the melt temperature of the material (i.e., the shot flow temperature as measured approaches or equals the melt temperature of the material).

In one embodiment, the cup 20 may be manufactured from an insulative material (e.g., a polymeric material, a ceramic material, etc.). By way of example, the cup 20 may be manufactured from polypropylene having a heat transfer speed of 0.07 British Thermal Units ("BTUs") per hour ("hr") or another polymer. The housing 40 and/or the locator 60 may be manufactured from a metallic material (e.g., steel, aluminum, hardened steel to improve wear resistance at a nozzle seat thereof or in another position, etc.).

The cup 20 may keep the material that is measured by the temperature probe 80 liquid or molten for longer (e.g., relative to systems that position a temperature probe 80 along the shot flow 110 but do not provide the cup 20, by reducing the flow of energy to the housing 40 or another heat sink, etc.), facilitating measurement of the shot flow temperature by the temperature probe 80. The shot flow 110 may travel through the barrel, platen, and/or other portions of the injection molding machine 100 as a non-Newtonian fluid.

Heat transfer may occur at the outer periphery of (e.g., radially outermost portion of, etc.) the shot flow 110 (i.e., the shot flow may cool or lose heat from the outside in). The heat transfer may produce solidification and the generation of a skin at one or more walls of the melt temperature sensing kit 10. Temperature probes may operate most accurately when inserted a target insertion depth into the material. By way of example, the target insertion depth may be ten times a diameter, a thickness, a width, etc. of the temperature probe. Measurement may occur at or near the tip of the temperature probe. The temperature probe 80 may thereby be configured to measure the temperature of the shot flow 110 within a region of the shot flow 110 that cools or loses heat first (e.g., relative to the inner volume of the shot flow, etc.). The cup 20 may facilitate accurate measurement of the shot flow temperature by keeping the outer periphery of the shot flow 110 molten for longer by reducing (e.g., eliminating, limiting, etc.) heat transfer therefrom into other components of the melt temperature sensing kit 10 and/or the injection molding machine 100. The cup 20 may additionally or alternatively facilitate accurate measurement of the shot flow temperature by separating the tip of the temperature probe 80 from the housing 40 (e.g., reducing the risk of the temperature probe 80 measuring the temperature of the housing 40 rather than the material, etc.).

In some embodiments, the cup 20 is configured to position the temperature probe 80 at an angle relative to a primary axis (e.g., a longitudinal axis, etc.) of the cup 20. The cup 20 may thereby position the temperature probe 80 to increase (e.g., maximize, etc.) the insertion depth of the temperature probe 80 within the shot flow 110. Increasing or decreasing the insertion depth may improve the accuracy of the temperature probe 80.

In some embodiments, the injection molding machine 100 is configured to provide the shot flow 110 for a period of 2-30 seconds. The shot flow temperature may be measured during the duration of the shot flow 110 (e.g., for the entire 2-30 second period, etc.). In one embodiment, the maximum shot flow temperature is recorded (e.g., on a master setup sheet based on readings provided by the pyrometer 82, etc.). The maximum shot flow temperature as measured using the melt temperature sensing kit 10 may approach or equal the melt temperature of the material. The maximum shot flow temperature may be utilized as a reference that is matched when pressures are changed and/or temperature variability inputs are adjusted (e.g., heater band settings, screw RPM, back pressure, screw design, residence time, etc.). The maximum shot flow temperature may be used to provide structurally similar products at different times. Recordation of the maximum shot flow temperature may also be used to provide documentation that the material was processed within manufacturer guidelines (i.e., proof for the molder that the product was properly processed within the recommendations of the resin supplier should concerns arise over brittle or weak products, etc.).

According to the exemplary embodiment shown in FIG. 3, the melt temperature sensing kit 10 is configured to be received by a portion of the injection molding machine 100. As shown in FIG. 3, the housing 40 defines a periphery, shown as periphery 42, that is configured to be received by a locating ring 120 of a platen 130 of the injection molding machine 100. In one embodiment, the periphery 42 of the housing 40 is generally circular. The periphery 42 may have a diameter of 3.980 inches (e.g., for receipt in a locating ring 120 having a diameter of 4.000 inches, etc.). In other embodiments, the periphery 42 is configured to be received by another portion of the platen 130. In one embodiment, the platen 130 is a stationary platen of the injection molding machine 100. As shown in FIG. 3, at least a portion of the melt temperature sensing kit 10 is disposed between a nozzle 140 and a mold 150. In one embodiment, the housing 40 includes one or more couplers (e.g., magnets, etc.) configured to facilitate engagement of the housing 40 with the mold 150 and/or the locating ring 120. The nozzle 140 may provide material into the mold 150 to produce injection molded products as part of an injection molding process. The melt temperature sensing kit 10 is positioned to and/or configured to receive the shot flow 110 from the nozzle 140 under conditions that are similar to (e.g., identical to, etc.) the conditions under which the injection molding machine 100 produces injection molded products. According to the exemplary embodiment shown in FIG. 3, the melt temperature sensing kit 10 at least partially defines a flow path, shown as flow path 160. The melt temperature sensing kit 10 may be configured to redirect the shot flow 110 along the flow path 160. At least one of the housing 40 and the cup 20 are configured (e.g., shaped, sized, etc.) to position the temperature probe 80 along the flow path 160 and thereby facilitate measurement of the shot flow temperature as part of the melt temperature measurement process.

In one embodiment, the shot flow 110 along the flow path 160 wipes material from the temperature probe 80. Wiping material from the temperature probe 80 may improve the likelihood of new material (i.e., material from upstream of the temperature probe 80) interacting with the temperature probe 80 and thereby increase the accuracy of the shot flow temperature measurement. In one embodiment, the cup 20 is configured to (e.g., positioned to, defines one or more apertures in a location to, etc.) facilitate wiping of the temperature probe by the shot flow 110.

The melt temperature sensing kit 10 is configured to position the cup 20 and the temperature probe 80 along the flow path 160 for measurement of the shot flow temperature. The shot flow 110 may be similar to (e.g., identical to, etc.) the flow of material provided by the injection molding machine 100 during the production of injection molded products. The position of the melt temperature sensing kit 10 as a whole, the cup 20, and/or the temperature probe 80 (e.g., along a material flow path through which the injection molding machine 100 provides material during the production of injection molding products, within the injection molding machine 100, etc.) facilitates accurate measurement of the shot flow temperature. In one embodiment, the position of the melt temperature sensing kit 10 as a whole, the cup 20, and/or the temperature probe 80 facilitates measurement of the shot flow temperature under conditions that are similar to (e.g., identical to, etc.) the conditions under which the injection molding machine 100 produces injection molded products. By way of example, a heater band setting, an injection pressure, a back pressure, a residence time, a screw RPM, and/or a screw-design-related condition may impact the melt temperature of the material.

The injection molding machine 100 may be cycled, run, or otherwise warmed up (e.g., in auto mode, etc.) until one or more the conditions have stabilized (e.g., to stabilize the melt, etc.). The barrel of the injection molding machine 100 may be withdrawn, removing the nozzle 140 from the locating ring 120. The melt temperature sensing kit 10 may be positioned, and the barrel of the injection molding machine 100 may be brought forward, bringing the nozzle 140 into engagement with the melt temperature sensing kit 10. A shot flow 110 may thereafter be initiated under conditions that are similar to the conditions the injection molding machine 100 produces injection molded parts (e.g., with an equal heater band setting, an identical injection pressure, the same back pressure, an appropriate residence time, a consistent screw RPM, and using the same screw, etc.), and the shot flow temperature may be measured. The melt temperature sensing kit 10 may be thereafter removed from the injection molding machine 100, and the temperature probe 80 may be removed from the housing 40. Another shot flow temperature may be taken using the melt temperature sensing kit 10 by removing the solidified shot flow 110 and the cup 20 and inserting a new cup 20 into the housing 40. The melt temperature sensing kit 10 positions the temperature probe 80 such that the shot flow temperature measurement occurs in-situ and/or in-line. By measuring the shot flow temperature under similar conditions as those used to produce injection molded products and in-situ and/or in-line, the melt temperature sensing kit 10 facilitates accurate measurement of the shot flow temperature.

The melt temperature sensing kit 10 may provide more accurate shot flow temperature measurement data than systems measuring a shot that is provided to the bed or table of the injection molding machine 100 and thereafter measured with a temperature probe. Such systems may measure the temperature of the material under conditions that are different than those used by the injection molding machine 100 to produce injection molded products (e.g., different back pressure, different RPMs, etc.). Such systems may also be susceptible to error induced due to heat transfer from the material on the bed or table into an ambient environment. The melt temperature sensing kit 10 positions the cup 20 and/or the temperature probe 80 within the injection molding machine 100 and thereby increases the accuracy of the shot flow temperature measurement.

The melt temperature sensing kit 10 may additionally or alternatively facilitate measurement of the shot flow temperature of shot flows provided by two or more different injection molding machines 100. By way of example, different injection molding machines 100 may operate under different conditions (e.g., different equal heater band settings or characteristics, different injection pressures, different back pressures, different RPMs, have different screw designs, etc.). The melt temperature sensing kit 10 facilitates measurement of the shot flow temperature independent of the various conditions under which the different injection molding machines 100 may operate. A target melt temperature or a target melt temperature range may be retrieved (e.g., by an operator from a lookup table, from a memory, etc.), and one or more operating conditions of the particular injection molding machine 100 may be adjusted (e.g., iteratively, etc.) such that the shot flow temperature approaches, equals, or falls within the target melt temperature or the target melt temperature range. This process may be repeated for two or more different machines to verify that injection molded products from the two or more different machines were produced using the same or similar melt temperature. The melt temperature sensing kit 10 may thereby facilitate the production of injection molded products having the same or similar characteristics (e.g., impact strength, tensile strength, etc.) and/or the flow characteristics of the material through the molds 150 using two or more injection molding machines 100.

As shown in FIGS. 3-7, the cup 20 has a proximate end 22 and a distal end 24 and includes a base, shown as base 26, and a sidewall, shown as sidewall 28. The base may enclose the distal end of the cup 20 and/or the sidewall 28, and the sidewall 28 may extend from the base 26. In one embodiment, at least one of the base 26 and the sidewall 28 are configured to be received by the housing 40. According to the exemplary embodiment shown in FIGS. 3-7, the cup 20 includes a sleeve, shown as sleeve 30. As shown in FIGS. 3-7, the sleeve 30 extends outward from the sidewall 28 of the cup 20. The sleeve 30 cooperates with the sidewall 28 to insulate the shot flow 110 and facilitate a shot flow temperature measurement by the temperature probe 80, according to an exemplary embodiment. In other embodiments, the cup 20 does not include the sleeve 30. The housing 40 and/or the locator 60 may have one or more features that differ (e.g., in shape, in size, etc.) from those shown in FIGS. 1-17 in embodiments where the cup 20 does not include the sleeve 30.

According to the exemplary embodiment shown in FIGS. 3-7, the sidewall 28 defines a first aperture, shown as opening 32, a second aperture, shown as passage 34, and an internal volume, shown as interior 36. The passage 34 may have a size (e.g., diameter, etc.) of 0.060 inches. In one embodiment, the opening 32 is defined by the sidewall 28 at the proximate end 22 of the cup 20, and the passage 34 is defined by the sidewall 28 between the proximate end 22 and the distal end 24 of the cup 20 such that the shot flow 110 travels through a length (e.g., the entire length, etc.) of the cup 20 prior to exiting therefrom. In other embodiments, the base 26 defines the passage 34. As shown in FIG. 3, the sleeve 30 defines an internal volume, shown as interior 38. The opening 32, the passage 34, the interior 36, and the interior 38 cooperate to define a portion of the flow path 160, according to the exemplary embodiment. At least a portion of the shot flow 110 may interface with the base 26 of the cup 20 and thereafter flow through the passage 34 and into the sleeve 30.

Figure 8:
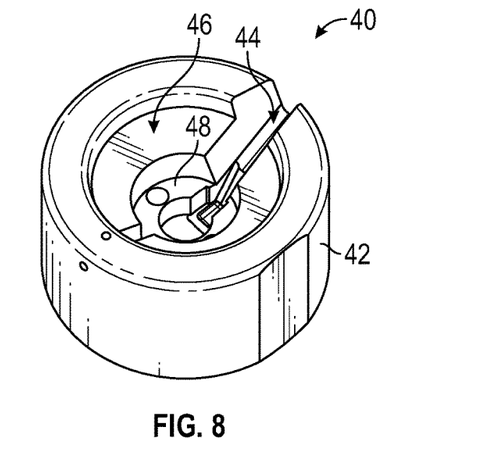
FIG. 8 is a perspective view of a housing of the melt temperature sensing kit of FIG. 1, according to an exemplary embodiment.
Figure 11:
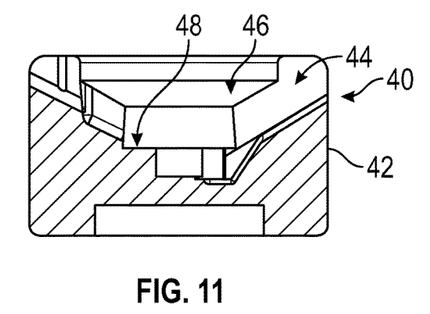
FIG. 11 is a sectional view of the housing of FIG. 8, according to an exemplary embodiment.
Figure 12:
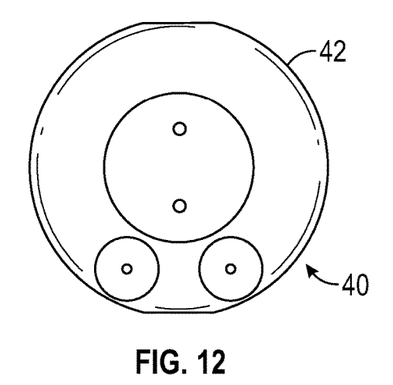
FIG. 12 is a bottom plan view of the housing of FIG. 8, according to an exemplary embodiment.
Figure 13:
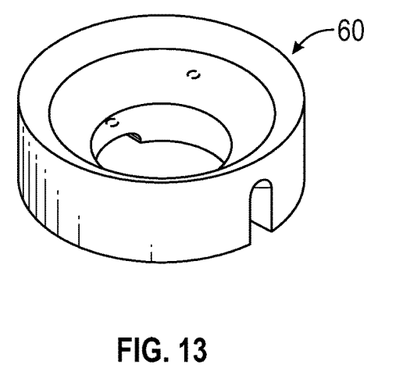
FIG. 13 is a perspective view of a locator of the melt temperature sensing kit of FIG. 1, according to an exemplary embodiment.
Figure 14:
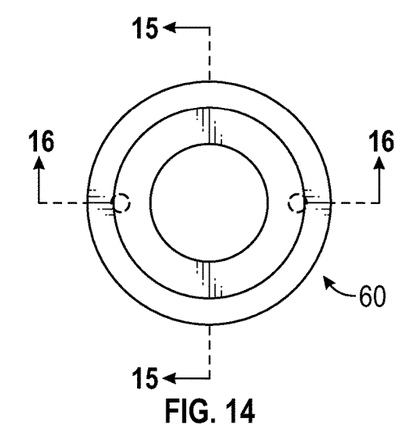
FIG. 14 is a top plan view of the locator of FIG. 13, according to an exemplary embodiment.
Figure 15:
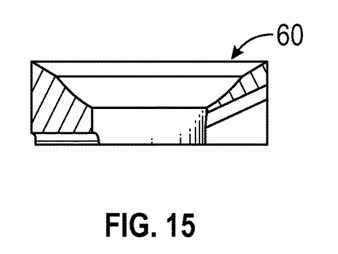
FIG. 15 is a sectional view of the locator of FIG. 13, according to an exemplary embodiment.

As shown in FIGS. 3, 8, and 11, the housing 40 defines a third aperture, shown as channel 44. The channel 44 may extend laterally inward (e.g., radially inward, etc.) from the periphery 42. In one embodiment, the channel 44 defines at least a portion of the flow path 160. By way of example, a shot flow may travel through the interior 36 and the sleeve 30 of the cup and out to an ambient environment (e.g., an environment within which the injection molding machine 100 is disposed, etc.) through the channel 44.

Figure 4:
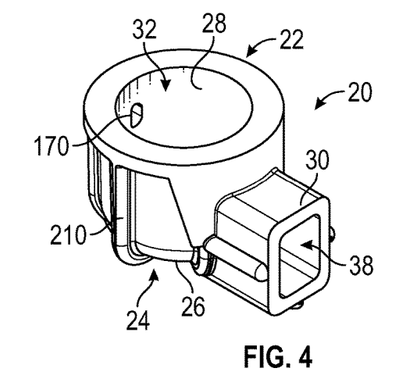
FIG. 4 is a perspective view of a cup of the melt temperature sensing kit of FIG. 1, according to an exemplary embodiment.
Figure 6:
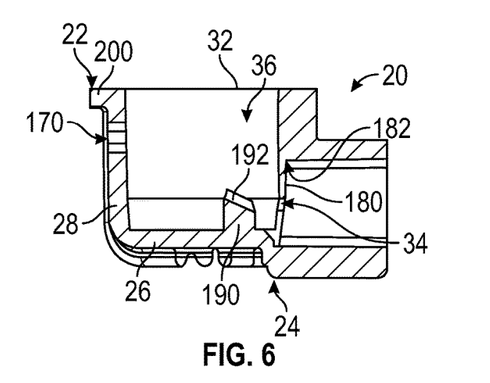
FIG. 6 is a sectional view of the cup of FIG. 4, according to an exemplary embodiment.

According to the exemplary embodiment shown in FIGS. 3, 4, and 6, the cup 20 defines a fourth aperture, shown as aperture 170. The aperture 170 may have a size (e.g., diameter, etc.) of 0.060 inches. In one embodiment the sidewall 28 of the cup 20 defines the aperture 170. As shown in FIG. 3, the passage 34 and the aperture 170 are positioned to receive the temperature probe 80. The temperature probe 80 may extend through the aperture 170, through the interior 36 of the cup 20, and through the passage 34. In other embodiments, the temperature probe 80 extends through the aperture 170 and only into the interior 36 (i.e., the cup 20 may not define the passage 34 and/or the temperature probe 80 may not extend through the passage 34). In still other embodiments, the cup 20 does not define the aperture 170. By way of example, the temperature probe 80 may extend into the interior 36 of the cup 20 through the passage 34 and/or through the sleeve 30.

As shown in FIGS. 3 and 8-12, the housing 40 defines a cavity, shown as cavity 46. In one embodiment, the cup 20 is configured to be received within at least a portion of the cavity 46 defined by the housing 40. In other embodiments, the housing 40 is configured (e.g., shaped, etc.) to receive the cup 20.

As shown in FIGS. 1-3, the cup 20 is configured to be received within at least a portion of the cavity 46 and interfaces with (e.g., is received by, contacts, engages, etc.) the locator 60. In one embodiment, the locator 60 provides hoop strength for the cup 20 and directs the shot flow 110 into the cup 20. The cup 20 may interface with the locator 60, and the locator 60 may interface with the housing 40. By way of example, the cup 20 may engage the locator 60 with a press-fit connection, and the locator 60 may engage the housing 40 with a slip fit connection. In one embodiment, the locator 60 is configured to hold the cup 20 within the cavity 46.

Figure 9:
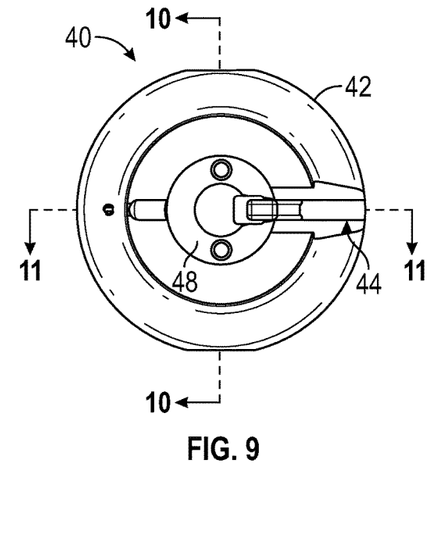
FIG. 9 is a top plan view of the housing of FIG. 8, according to an exemplary embodiment.
Figure 10:
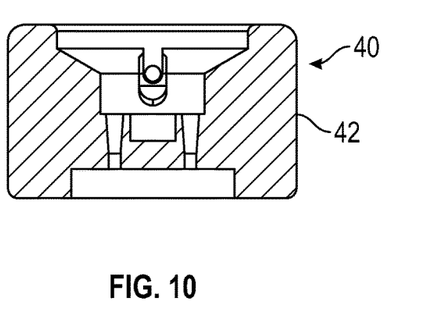
FIG. 10 is a sectional view of the housing of FIG. 8, according to an exemplary embodiment.
Figure 16:
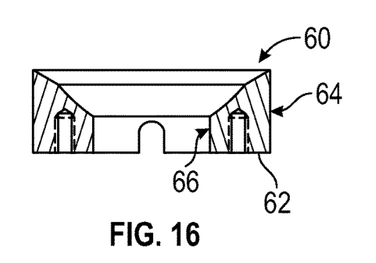
FIG. 16 is a sectional view of the locator of FIG. 13, according to an exemplary embodiment.
Figure 17:
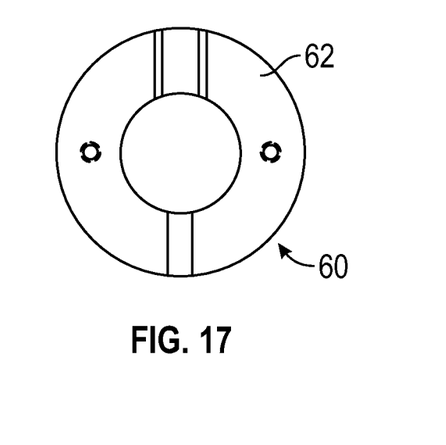
FIG. 17 is a bottom plan view of the locator of FIG. 13, according to an exemplary embodiment.

As shown in FIGS. 8, 9, and 11, the housing 40 includes a ledge, shown as ledge 48. The locator 60 may be inserted into the cavity 46 and into engagement with the ledge 48 (e.g., to position the locator 60 within the housing 40, etc.). As shown in FIGS. 3, 16, and 17, the locator 60 defines a bottom surface 62 that interfaces with the ledge 48 (e.g., when the locator 60 is seated within the housing 40, etc.). In one embodiment, the locator 60 defines an outer periphery 64 having a shape that corresponds with a portion of the housing 40 (e.g., the portion of the housing 40 that receives the locator 60, etc.). The locator 60 may be annular. In one embodiment, the locator 60 defines an inner periphery 66 having a shape that corresponds with at least a portion of the cup 20.

According to the exemplary embodiment shown in FIGS. 3 and 6, the cup 20 includes a door, shown as door 180. The door is positioned along the flow path 160, according to an exemplary embodiment. In one embodiment, the door 180 defines at least a portion of the passage 34. In another embodiment, the sleeve 30 at least partially surrounds the door 180 and the passage 34.

The door 180 may be configured (e.g., shaped, sized, positioned, etc.) to provide a buildup of material within the cup 20. In one embodiment, the door 180 slows down an initial front of the shot flow 110. Slowing down the shot flow 110 may facilitate measurement of the shot flow temperature of the initial portion of the shot flow 110. By way of example, the initial portion of the shot flow 110 may travel through the passage 34, and the temperature thereof may be measured at the tip of the temperature probe 80.

The door 180 may additionally or alternatively produce back pressure within the cup 20 during an initial period of the shot flow 110. The door 180 may provide back pressure as the initial front of the shot flow 110 is received by the cup 20 and/or travels through the passage 34. At least due to the production of back pressure within the cup 20, the door 180 may be configured to facilitate packing the shot flow 110 around the temperature probe 80. Packing the shot flow 110 around the temperature probe 80 may facilitate measurement of the shot flow temperature (e.g., such that the shot flow temperature as measured by the temperature probe 80 approaches and/or equals the melt temperature of the material, etc.).

The door 180 may additionally or alternatively extend the solidification time of the shot flow 110 by providing the buildup of material (e.g., a plug, a purge, etc.) within the cup 20. By way of example, the buildup of material may produce a larger volume of material within the cup 20 for an extended period of time. A measured region (e.g., the middle, etc.) of the larger volume of material within the cup 20 may be kept liquid or molten for a longer period of time (e.g., as the material may first cool or lose heat at the outer regions thereof, etc.). In response to opening the door 180, the shot flow 110, under backpressure, may abruptly flow into the sleeve 30, and the influx of liquid or molten material into the sleeve 30 may keep the material within the sleeve 30 liquid or molten for longer. The door 180 may thereby improve the accuracy of the shot flow temperature measurement.

In one embodiment, the door 180 facilitates use of the melt temperature sensing kit 10 with different shot sizes (e.g., different volumes of the shot flow 110, etc.). The door 180 may retain smaller shot sizes and produce a buildup of material within the cup 20 such that the shot flow 110 packs around the temperature probe 80. The door 180 may also facilitate use of the melt temperature sensing kit 10 with larger shot sizes and produce a buildup of material within the cup 20 that is released upon opening of the door 180. The door 180 may be configured to open earlier (e.g., at a shorter elapsed time relative to the shot initiation time, etc.) when the melt temperature sensing kit 10 is utilized with larger shot sizes than with smaller shot sizes.

The door 180 may additionally or alternatively be configured to facilitate preheating a body portion of the temperature probe 80 (e.g., by facilitating packing the shot flow 110 around the temperature probe 80, etc.). In one embodiment, the body portion of the temperature probe 80 includes a length of the temperature probe 80 equal to at least ten times the diameter of the temperature probe 80 (e.g., 0.600 inches in one embodiment where the temperature probe 80 has a diameter of 0.060 inches, etc.). By way of example, the door 180 may facilitate preheating the portion of the temperature probe 80 that is disposed within (e.g., extends through, etc.) interior 36 of the cup 20. In some embodiments, the temperature probe 80 is configured to measure the shot flow temperature at or near the tip of the temperature probe 80. Preheating the body portion of the temperature probe 80 (e.g., with the door 180 by way of backpressure and/or packing, etc.) may reduce heat transfer from the tip of the temperature probe 80 and facilitate accurate measurement of the shot flow temperature.

In one embodiment, the door 180 is configured to open in response to an applied pressure by the shot flow 110 (e.g., the back pressure exceeding a threshold level, etc.). The door 180 may provide a supplemental passage defining at least a portion of the flow path 160 in response to opening. By way of example, one or more portions of the door 180 may fracture or otherwise fail to produce the supplemental passage.

According to the exemplary embodiment shown in FIG. 6, the door 180 is coupled to the sidewall 28 of the cup 20 with a hinge, shown as hinge 182. In other embodiments, the door 180 is otherwise coupled to the sidewall 28 of the cup 20. In still other embodiments, the door 180 is coupled to another portion of the cup 20. By way of example, the door 180 may be coupled to (e.g., span, etc.) an end of the sleeve 30 that is attached to the cup 20. By way of another example, the door 180 may be coupled to (e.g., span, etc.) an opposing second end of the sleeve 30 (e.g., an end of the sleeve 30 spaced from the sidewall 28 by a body of the sleeve 30, etc.).

In some embodiments, the hinge 182 is formed at one end of the door 180. In other embodiments, the hinge 182 is formed around at least a portion of a periphery of the door 180. The door 180 may have a thickness that is uniform, and the hinge may be defined at the coupling between the door 180 and the sidewall 28 of the cup 20. By way of example, the door 180 may have a thickness of 0.005-0.045 inches. In other embodiments, the door 180 has a first thickness, and the hinge 182 has a second thickness. By way of example, the door 180 may be thicker than the hinge 182 such that the hinge 182 is configured to fracture or otherwise fail in response to the backpressure within the cup 20 exceeding the threshold level. The door 180 may remain intact and/or may travel along the flow path 160 with the shot flow 110.

According to the exemplary embodiment shown in FIG. 6, the cup 20 includes a support, shown as support 190. In one embodiment, the support 190 holds, positions, and/or reinforces the temperature probe 80 during a melt temperature measurement process. As shown in FIG. 6, the support 190 extends from the base 26 and into the interior 36 of the cup 20. In one embodiment, the support 190 has an end 192 configured to engage the temperature probe 80. By way of example, the end 192 may define a contour that corresponds with a profile (e.g., a circular cross-sectional shape, etc.) of the temperature probe 80 (e.g., as received within the cup 20, etc.). In some embodiments, the cup 20 is configured to physically protect the temperature probe 80 from damage. By way of example, the support 190 may reduce the risk of the temperature probe 80 bending or otherwise becoming damaged due to the shot flow 110, insertion into the housing 40, removal from the housing 40, etc. Support 190 may particularly protect thin temperature probes 80.

Figure 5:
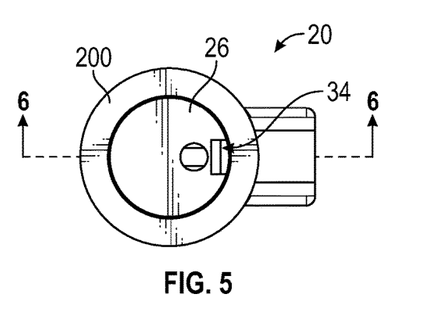
FIG. 5 is a top plan view of the cup of FIG. 4, according to an exemplary embodiment.
Figure 7:
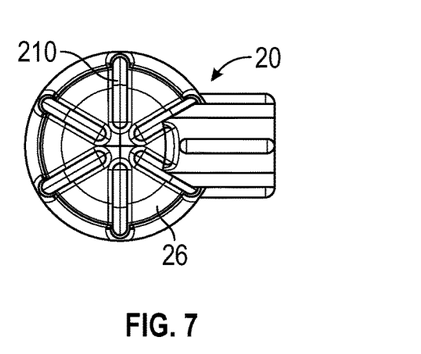
FIG. 7 is a bottom plan view of the cup of FIG. 4, according to an exemplary embodiment.

As shown in FIGS. 5 and 6, the cup 20 includes a rim, shown as rim 200. The rim 200 is coupled to the sidewall 28, according to an exemplary embodiment, and positioned at the proximate end 22 of the cup 20. The cup 20 includes a plurality of ribs 210, according to the exemplary embodiment shown in FIGS. 4 and 7. As shown in FIGS. 4 and 7, the plurality of ribs 210 extend outward from the base 26 and the sidewall 28. In one embodiment, the rim 200 and/or the plurality of ribs 210 cooperate to space the sidewall 28 of the cup 20 from other components of the melt temperature sensing kit 10 (e.g., from the locator 60, from the housing 40, etc.). The rim 200 and/or the plurality of ribs 210 are thereby configured to facilitate accurate measurement of the shot flow temperature by further isolating and/or insulating the molten shot flow 110 within the cup 20 from heat transfer to the components (e.g., metallic components, etc.) of the melt temperature sensing kit 10 (e.g., to provide an air gap therebetween, etc.). The rim 200 and/or the plurality of ribs 210 may thereby reduce the risk of the shot flow 110 solidifying prematurely (e.g., before accurate measurement of the shot flow temperature, etc.) and/or otherwise increase the accuracy of the shot flow temperature measurement.

Figure 18:
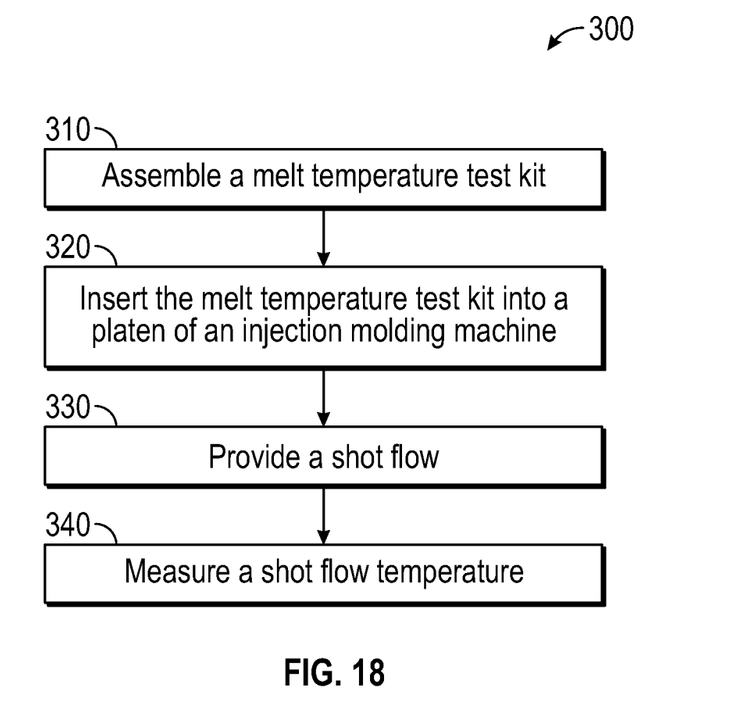
FIG. 18 is schematic representation of a melt temperature measurement process, according to an exemplary embodiment.

According to the exemplary embodiment shown in FIG. 18, a melt temperature measurement process, shown as process 300, is used to measure a shot flow temperature of a shot flow during an injection molding process. As shown in FIG. 18, the process 300 includes assembling a melt temperature sensing kit at step 310. In one embodiment, the melt temperature sensing kit includes a temperature probe. In other embodiments, an operator provides the temperature probe and/or a pyrometer for use with the melt temperature sensing kit.

As shown in FIG. 18, the process 300 includes inserting the melt temperature sensing kit into a platen of an injection molding machine at a step 310. In one embodiment, inserting the melt temperature sensing kit inserting the melt temperature sensing kit at the step 320 includes inserting a housing of the melt temperature sensing kit into a stationary platen of an injection molding machine. The process 300 includes a shot flow at a step 330, according to the exemplary embodiment shown in FIG. 18. In one embodiment, providing the shot flow at the step 330 includes providing the shot flow through the melt temperature sensing kit with the injection molding machine. As shown in FIG. 18, the process 300 includes measuring a shot flow temperature at a step 340. Measuring the shot flow temperature at the step 340 may include measuring the shot flow temperature of the shot flow with the temperature probe of the melt temperature sensing kit. According to an exemplary embodiment, the process 300 further includes removing a melt temperature test cup from at least one of a retainer and a housing of the melt temperature sensing kit, inserting a second melt temperature test cup into at least one of the retainer and the housing of the melt temperature sensing kit, inserting the melt temperature sensing kit into a platen of a second injection molding machine, providing a second shot flow through the melt temperature sensing kit with the second injection molding machine, and measuring a shot flow temperature of the second shot flow with the temperature probe of the melt temperature sensing kit.

As utilized herein, the terms "approximately", "about", "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as may be recited in appended claims.

It should be noted that the terms "exemplary" and "example" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like, as used herein, mean the joining of two members directly or indirectly to one another. Such joining may be stationary (e.g., permanent, etc.) or moveable (e.g., removable, releasable, etc.). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," "between," etc.) are merely used to describe the orientation of various elements in the figures. It should be noted that the orientation of various elements may differ according to other exemplary embodiments, and that such variations are intended to be encompassed by the present disclosure.

It is important to note that the construction and arrangement of the melt temperature sensing kit as shown in the exemplary embodiments is illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. It should be noted that the elements and/or assemblies of the components described herein may be constructed from any of a wide variety of materials that provide sufficient strength or durability, in any of a wide variety of colors, textures, and combinations. Accordingly, all such modifications are intended to be included within the scope of the present inventions. Other substitutions, modifications, changes, and omissions may be made in the design, operating conditions, and arrangement of the preferred and other exemplary embodiments without departing from scope of the present disclosure or from the spirit of the appended claims.

The invention claimed is:

1. A melt temperature sensing kit, comprising:
a housing defining a cavity and having an outer periphery configured to be received by a platen of an injection molding machine; and
a cup having a proximate end and a distal end and configured to be received within at least a portion of the cavity, the cup comprising:
  a base enclosing the distal end of the cup; and
  a sidewall extending from the base, the sidewall defining a first aperture at the proximate end of the cup, a second aperture disposed between the proximate end and the distal end of the cup, and an internal volume, wherein the first aperture, the second aperture, and the internal volume cooperate to define a flow path,
wherein at least one of the housing and the cup are configured to position a temperature probe along the flow path and thereby facilitate measurement of a shot flow temperature as part of a melt temperature measurement process, wherein the housing defines a third aperture extending laterally inward from the outer periphery and forming a portion of the flow path, wherein the sidewall of the cup defines a fourth aperture, wherein the second aperture and the fourth aperture are positioned to receive the temperature probe, wherein the cup includes a door coupled to the sidewall with a hinge, and wherein the door at least partially defines the second aperture.

2. The melt temperature sensing kit of claim 1, wherein the sidewall is thicker than the hinge such that the hinge is configured to fail in response to an applied pressure produced during the melt temperature measurement process.

3. The melt temperature sensing kit of claim 1, wherein the cup includes a sleeve extending outward from the sidewall, wherein the sleeve is disposed along the flow path and at least partially surrounds the door and the second aperture.

4. A melt temperature sensing kit, comprising:
a housing defining a cavity and having an outer periphery configured to be received by a platen of an injection molding machine;
a CUP having a proximate end and a distal end and configured to be received within at least a portion of the cavity, the cup comprising:
  a base enclosing the distal end of the cup; and
  a sidewall extending from the base, the sidewall defining a first aperture at the proximate end of the cup, a second aperture disposed between the proximate end and the distal end of the cup, and an internal volume, wherein the first aperture, the second aperture, and the internal volume cooperate to define a flow path; and
a temperature probe,
wherein at least one of the housing and the cup are configured to position the temperature probe along the flow path and thereby facilitate measurement of a shot flow temperature as part of a melt temperature measurement process, wherein the housing defines a third aperture extending laterally inward from the outer periphery and forming a portion of the flow path, wherein the sidewall of the CUP defines a fourth aperture, and wherein the second aperture and the fourth aperture are positioned to receive the temperature probe.

5. The melt temperature sensing kit of claim 4, wherein the temperature probe includes a stop configured to interface with the housing and thereby limit insertion of the temperature probe to a target depth.

6. The melt temperature sensing kit of claim 4, wherein the cup includes a support extending from the base and into the internal volume defined by the sidewall, wherein the support has an end defining a contour that corresponds with a profile of the temperature probe.

7. A melt temperature sensing kit, comprising:
a housing defining a cavity and having an outer periphery configured to be received by a platen of an injection molding machine;
a cup having a proximate end and a distal end and configured to be received within at least a portion of the cavity, the cup comprising:
  a base enclosing the distal end of the cup; and
  a sidewall extending from the base, the sidewall defining a first aperture at the proximate end of the CUP, a second aperture disposed between the proximate end and the distal end of the cup, and an internal volume, wherein the first aperture, the second aperture, and the internal volume cooperate to define a flow path; and
a locator configured to hold the cup within the cavity,
wherein the locator defines an outer periphery having a shape that corresponds with a portion of the housing, and wherein the locator defines an inner periphery having a shape that corresponds with at least a portion of the cup, and wherein at least one of the housing and the CUP are configured to position a temperature probe along the flow path and thereby facilitate measurement of a shot flow temperature as part of a melt temperature measurement process.

8. The melt temperature sensing kit of claim 7, wherein the cup includes:
a rim coupled to the sidewall; and
a plurality of ribs extending outward from the sidewall.

9. The melt temperature sensing kit of claim 7, wherein the housing and the locator comprise a conductive material, and wherein the cup comprises an insulative material.

10. The melt temperature sensing kit of claim 9, wherein the housing and the locator comprise a metallic material, and wherein the cup comprises at least one of a polymeric material and a ceramic material.

* * * * *